(12) United States Patent
Aujla

(10) Patent No.: US 10,912,475 B2
(45) Date of Patent: Feb. 9, 2021

(54) CATHETER WITH SPLIT ELECTRODE SLEEVE AND RELATED METHODS

(71) Applicant: Biosense Webster (Israel ) LTD., Yokneam (IL)

(72) Inventor: Vishav Manak Singh Aujla, Valencia, CA (US)

(73) Assignee: BIOSENSE WEBSTER (ISRAEL) LTD, Yokneam (IL)

( * ) Notice: Subject to any disclaimer, the term of this patent is extended or adjusted under 35 U.S.C. 154(b) by 823 days.

(21) Appl. No.: 15/246,434

(22) Filed: Aug. 24, 2016

(65) Prior Publication Data
US 2018/0055562 A1 Mar. 1, 2018

(51) Int. Cl.
| | | |
|---|---|---|
| *A61B 5/042* | (2006.01) | |
| *A61B 5/00* | (2006.01) | |
| *A61B 18/14* | (2006.01) | |
| *A61B 17/00* | (2006.01) | |
| *A61B 18/00* | (2006.01) | |

(52) U.S. Cl.
CPC .......... *A61B 5/0422* (2013.01); *A61B 5/6852* (2013.01); *A61B 17/00234* (2013.01); *A61B 18/1492* (2013.01); *A61B 2017/00053* (2013.01); *A61B 2017/00323* (2013.01); *A61B 2017/00327* (2013.01); *A61B 2018/00083* (2013.01); *A61B 2018/00166* (2013.01); *A61B 2018/00351* (2013.01); *A61B 2018/00577* (2013.01); *A61B 2018/00839* (2013.01); *A61B 2018/1467* (2013.01); *A61B 2018/1497* (2013.01)

(58) Field of Classification Search
CPC ...... A61B 5/0422; A61B 18/1492; A61N 1/05
See application file for complete search history.

(56) References Cited

U.S. PATENT DOCUMENTS

| | | | |
|---|---|---|---|
| 5,788,692 A | 8/1998 | Campbell et al. | |
| 6,447,505 B2 * | 9/2002 | McGovern | A61B 18/1485 606/41 |
| 7,699,829 B2 * | 4/2010 | Harris | A61B 5/0422 604/264 |

(Continued)

FOREIGN PATENT DOCUMENTS

WO WO2017048965 * 3/2017

OTHER PUBLICATIONS

Extended European Search Report for European Application No. EP17187657, dated Jan. 17, 2018; 8 pages.

*Primary Examiner* — Lee S Cohen
(74) *Attorney, Agent, or Firm* — Etan S. Chatlynne; Roberts Calderon Safran & Cole P.C.

(57) ABSTRACT

An electrophysiology catheter having an electrode sleeve mounted on a distal section, the electrode sleeve comprising an electrically-nonconductive band and a plurality of discrete electrodes, the band extending circumferentially around the distal section, each discrete electrode occupying a different radial position around the band. The catheter includes a plurality of lead wires extending through the elongated body and the deflection section, and into the distal section, each lead wire passing through a respective aperture formed in the sidewall of the tubing of the distal section, each wire being connected at its distal end to a respective discrete electrode.

11 Claims, 10 Drawing Sheets

(56) References Cited

U.S. PATENT DOCUMENTS

| | | | |
|---|---|---|---|
| 8,000,808 B2* | 8/2011 | Hegland | A61B 5/0422 |
| | | | 600/393 |
| 8,287,532 B2 | 10/2012 | Carroll et al. | |
| 8,888,788 B2* | 11/2014 | Hakala | A61B 17/22022 |
| | | | 606/128 |
| 8,961,509 B2* | 2/2015 | Falwell | A61B 5/0422 |
| | | | 604/95.04 |
| 9,101,733 B2 | 8/2015 | McDaniel | |
| 9,907,480 B2* | 3/2018 | Basu | A61B 5/042 |
| 2004/0092806 A1* | 5/2004 | Sagon | A61B 5/0422 |
| | | | 600/374 |
| 2012/0123294 A1 | 5/2012 | Sun et al. | |
| 2013/0085360 A1 | 4/2013 | Grunewald | |
| 2014/0243640 A1* | 8/2014 | O'Dea | A61B 5/0084 |
| | | | 600/373 |
| 2015/0157401 A1* | 6/2015 | Falwell | A61B 5/0422 |
| | | | 606/41 |
| 2016/0183823 A1 | 6/2016 | Selkee | |
| 2017/0042613 A1* | 2/2017 | Schultheis | A61B 5/0422 |

* cited by examiner

CATHETER WITH SPLIT ELECTRODE SLEEVE AND RELATED METHODS

FIELD OF INVENTION

This invention relates to an electrophysiology catheter, in particular, a cardiac electrophysiology catheter with an electrode configuration that provides for more accurate and discrete sensing.

BACKGROUND

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Once the catheter is positioned within the heart, the location of aberrant electrical activity within the heart is then located.

One location technique involves an electrophysiological mapping procedure whereby the electrical signals emanating from the conductive endocardial tissues are systematically monitored and a map is created of those signals. By analyzing that map, the physician can identify the interfering electrical pathway. A conventional method for mapping the electrical signals from conductive heart tissue is to percutaneously introduce an electrophysiology catheter (electrode catheter) having mapping electrodes mounted on its distal extremity. The catheter is maneuvered to place these electrodes in contact with the endocardium. By monitoring the electrical signals at the endocardium, aberrant conductive tissue sites responsible for the arrhythmia can be pinpointed.

For mapping, it is desirable to have relatively small mapping electrodes. It has been found that smaller electrodes record more accurate and discrete electrograms because larger electrodes are susceptible to detecting both desirable near-field signals and undesirable far-field signals. When a portion of an electrode is not in contact with tissue, it is exposed to blood which can propagate far-field electrical signals from other regions of the heart. The far-field signals interfere with the near-field signals, making accurate measurement of the near-field signals difficult.

A conventional catheter 100 may have a tip electrode 117 and one or more ring electrodes 127 as shown in FIG. 1. The one or more ring electrodes 127 are susceptible to detecting far-field signals when the catheter is laid sideways against tissue because often half of each ring electrode may be out of contact with tissue T and thus exposed to blood, as shown in FIG. 1.

Smaller electrodes are also safer for ablation, that is, the application of RF (radio frequency) current to the electrodes to destroy the tissue causing the arrhythmia. As the temperature of an electrode increases during ablation, char and thrombus may form on the electrode and become dislodged from the electrode. The formation of char and thrombus may be detected by monitoring impedance of the electrode. With a relatively large electrode, an impedance rise from char and thrombus formation may not be easily detected because the char and thrombus are formed over a relatively small percentage of the total surface area of the electrode. In contrast, if the electrically active surface area of the electrode is relatively small, char and thrombus will form over a relatively larger area of the electrode, making detection by impedance measurements easier.

For electrophysiology catheters with more complex distal electrode configurations, such as those with multiple spine members carrying a multitude of ring electrodes, there is a greater risk of spines touching which could potentially cause the ring electrodes to short circuit. By reducing the active surface of the ring electrodes, the risk of the ring electrodes short-circuiting can be reduced.

Accordingly, a need exists for an electrophysiology catheter with electrodes having relatively small surface areas and an electrode configuration that maximizes tissue contact for more accurate measurement of near-field activity even when the catheter is laid sideways against tissue. There is also a need for a method of manufacture of such an electrophysiology catheter that simplifies the assembly and wiring of smaller electrodes on the circumferential surface of the catheter distal section.

SUMMARY OF THE INVENTION

The present invention is directed to an electrophysiology catheter with electrodes having relatively small surface areas and an electrode configuration that maximizes tissue contact for more accurate measurement of near-field activity even when the catheter is laid sideways against tissue. The electrophysiology catheter construction simplifies the assembly and wiring of smaller electrodes on the circumference surface of the catheter distal section.

In some embodiments, the electrophysiology catheter comprises an elongated body, a distal section distal of the elongated body, and an electrode sleeve mounted on the distal section. The electrode sleeve has a band extending circumferentially around the distal section, the band being constructed of an electrically-nonconductive material, and a plurality of discrete electrodes affixed to the band, each occupying a different radial position around the band.

In more detailed embodiments, each discrete electrode has an overhang edge portion to provide a surface for lead wire attachment.

In more detailed embodiments, the catheter may have between about two and eight discrete electrodes.

In more detailed embodiments, the catheter includes a puller wire, wherein the puller wire is longitudinally aligned with at least one discrete electrode.

In more detailed embodiments, each discrete electrode has a curved outer surface and the plurality of discrete electrodes are arranged on the band such that their curved outer surfaces trace a circumference around the band.

In other embodiments, electrophysiology catheter comprising an elongated body, a deflection section distal of the elongated body, a distal section distal of the elongated body, the distal section having a tubing with a sidewall, and an electrode sleeve mounted on the distal section, the electrode sleeve comprising an electrically-nonconductive band and a plurality of discrete electrodes, the band extending circumferentially around the distal section, each discrete electrode occupying a different radial position around the band. The catheter includes a plurality of lead wires extending through the elongated body and the deflection section, and into the distal section, each lead wire passing through a respective aperture formed in the sidewall of the tubing of the distal section, each wire being connected at its distal end to a respective discrete electrode.

The present invention also includes a method of assembling the aforementioned catheter, the method comprising: forming the respective aperture for each lead wire in the sidewall of the distal section; passing each lead wire in the distal section through a respective aperture to outside of the distal section; connecting a distal end of each lead wire to a respective discrete electrode on the electrode sleeve; and sliding the electrode sleeve onto the distal section.

In some embodiments, the connecting a distal end of each lead wire includes connecting the distal end of each lead wire to an overhang edge portion of each discrete electrode.

In some embodiments, the method includes positioning the electrode sleeve on the distal section such that the overhang edge portions are radially aligned with the apertures.

In some embodiments, the catheter includes at least one puller wire extending therethrough, and the method includes positioning the electrode sleeve on the distal section such that at least one discrete electrode is longitudinally aligned with the puller wire.

The present invention also includes a method of manufacturing the electrode sleeve of claim 7, comprising: providing a die having an outer die and an inner die; placing the discrete electrodes between the outer die and the inner die; and filling the die with a thermoplastic material.

In some embodiment, the filling the die forms the electrode sleeve via injection-molding.

In some embodiments, the filling the die forms the electrode sleeve via over-molding.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
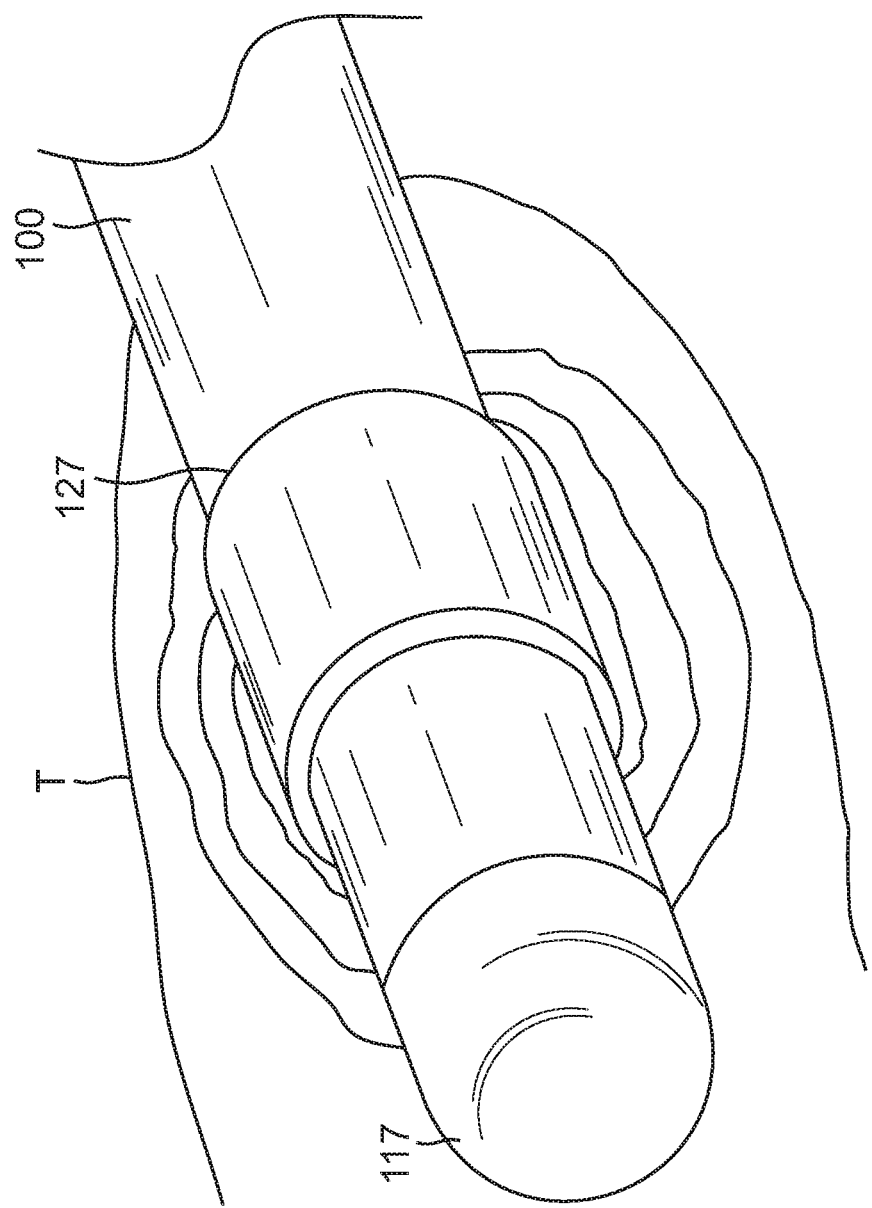
FIG. 1 is a perspective view of a distal section of a catheter having a distal tip electrode and a ring electrode as known in the prior art.
Figure 2:
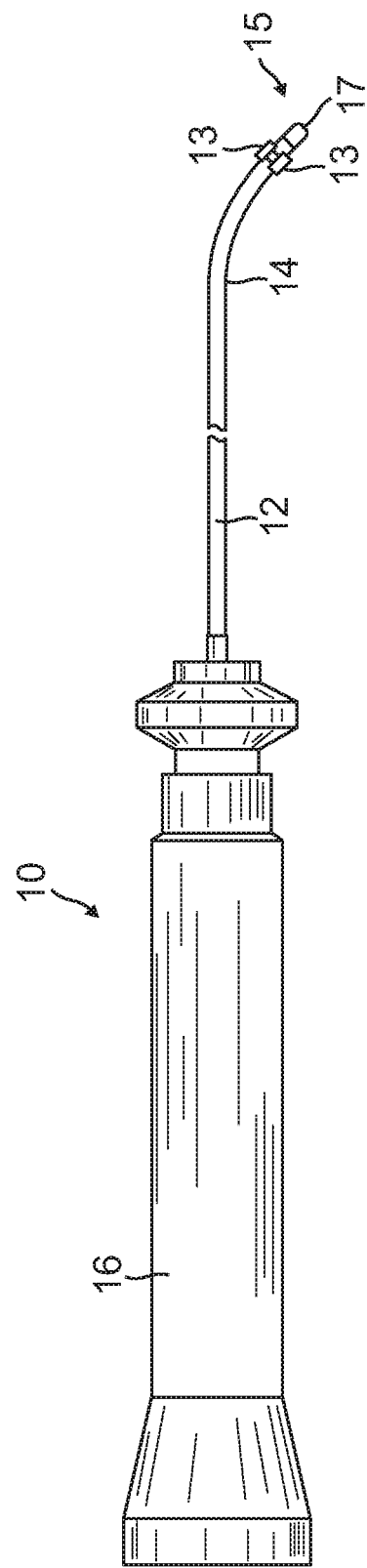
FIG. 2 is a side view of a catheter of the present invention, in accordance with an embodiment.
Figure 3:
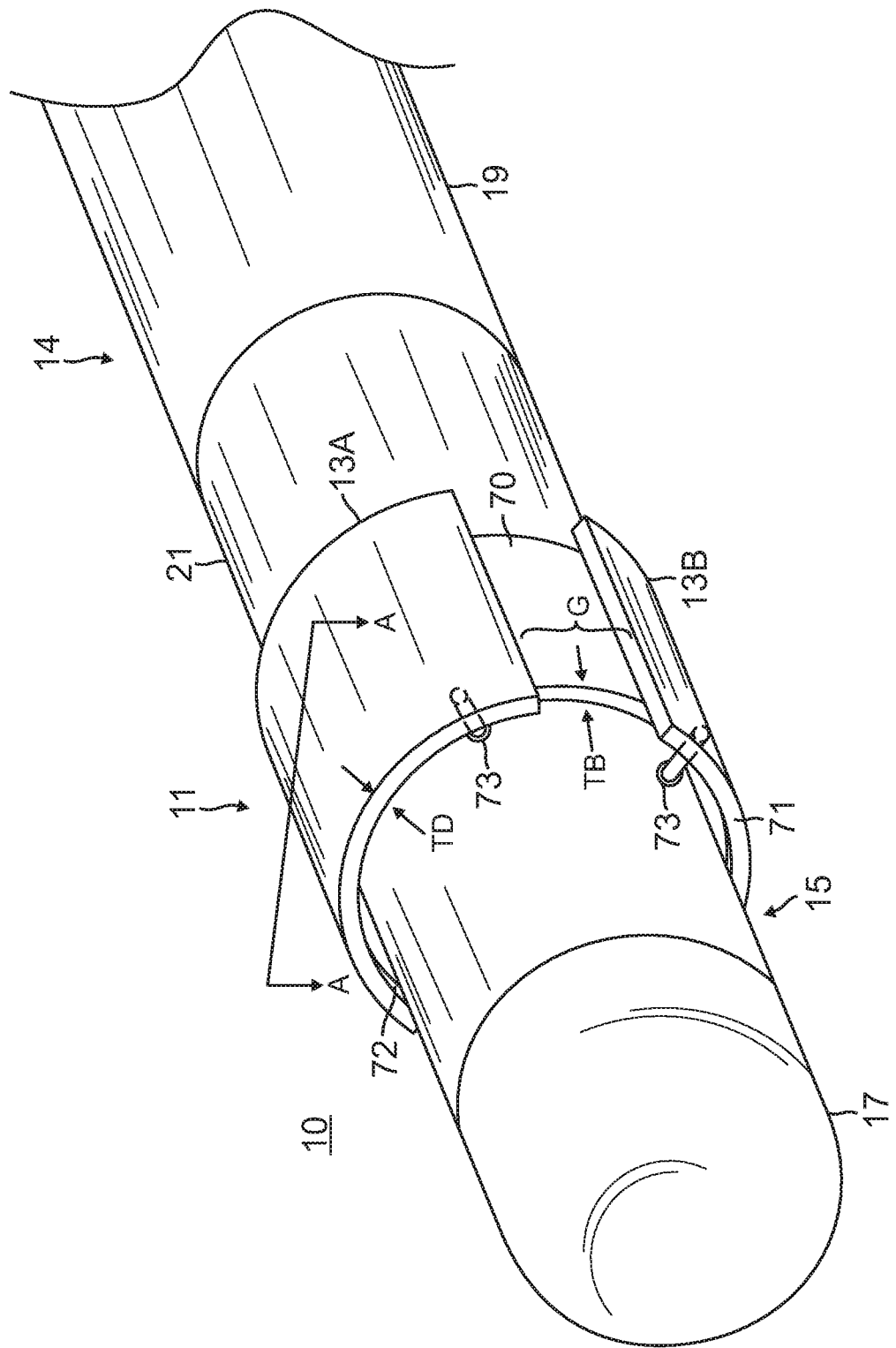
FIG. 3 is a perspective view of a distal section of the catheter of FIG. 2.

Referring to FIG. 2 and FIG. 3, the present invention includes a catheter 10 with a split electrode sleeve 11 adapted for discrete electrode tissue contact and minimized exposure to blood. In some embodiments, the catheter comprises a catheter body 12, an intermediate deflection section 14, a distal end section 15, and a control handle 16 proximal of the catheter body 12. In some embodiments, the split electrode sleeve 11 has a band 70 and a plurality of discrete electrodes 13, and the sleeve 11 is carried on the distal end section 15, proximal of a distal end or distal tip electrode 17.

Figure 4:
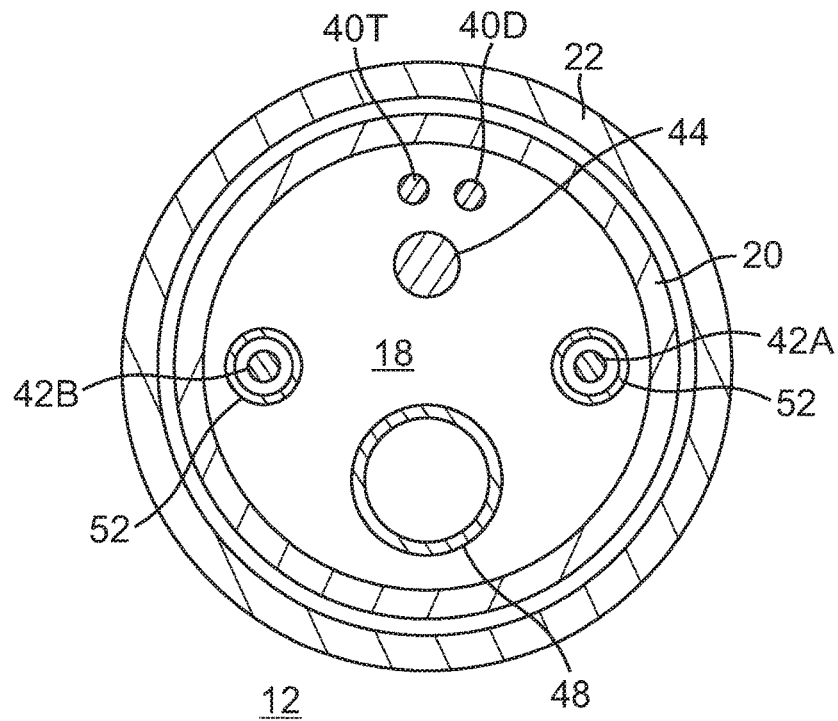
FIG. 4 is an end cross-sectional view of a catheter body of the catheter of FIG. 1.

The catheter body 12 comprises an elongated tubular construction, having a single, axial or central lumen 18, as shown in FIG. 2 and FIG. 4. The catheter body 12 is flexible, i.e., bendable, but substantially non-compressible along its length. The catheter body 12 can be of any suitable construction and made of any suitable material. A presently preferred construction comprises an outer wall 22 made of a polyurethane, or PEBAX. The outer wall 22 comprises an imbedded braided mesh of high-strength steel, stainless steel or the like to increase torsional stiffness of the catheter body 12 so that, when the control handle 16 is rotated, the tip section 14 of the catheter 10 will rotate in a corresponding manner.

The outer diameter of the catheter body 12 is not critical, but is preferably no more than about 8 french, more preferably about 7 french. Likewise the thickness of the outer wall 22 is not critical, but is thin enough so that the central lumen 18 can accommodate components, including, for example, one or more puller wires, electrode lead wires, irrigation tubing, and any other wires and/or cables. The inner surface of the outer wall 22 is lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing is presently preferred for the stiffening tube 20 because it may be very thin walled while still providing very good stiffness. This maximizes the diameter of the central lumen 18 without sacrificing strength and stiffness. As would be recognized by one skilled in the art, the catheter body construction can be modified as desired. For example, the stiffening tube can be eliminated.

Figure 5:
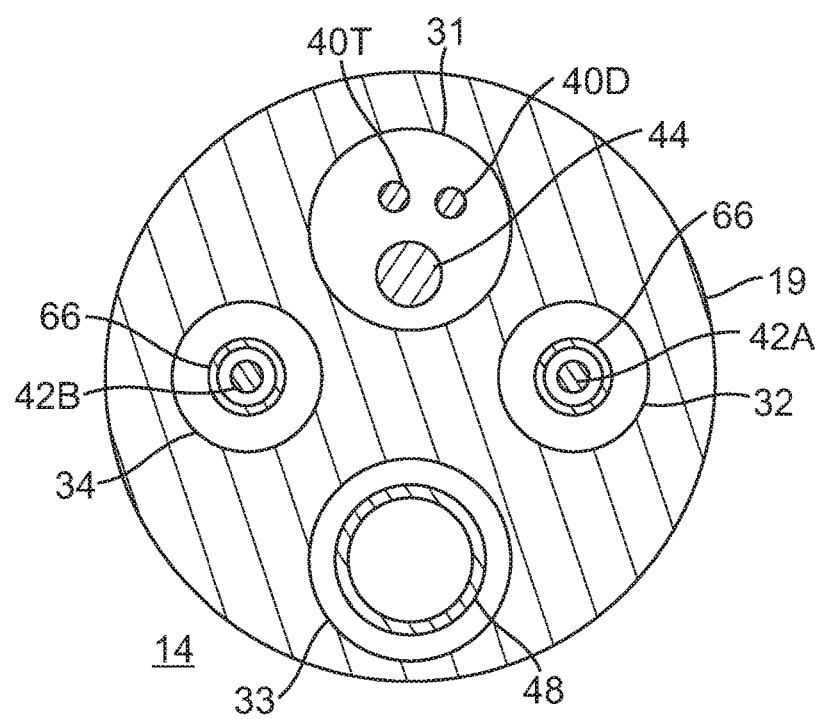
FIG. 5 is an end cross-sectional view of an intermediate deflection section of the catheter of FIG. 1.

The intermediate deflection section comprises a shorter section of tubing 19, which as shown in FIG. 3 and FIG. 5, has multiple lumens, for example, off-axis lumens 31, 32, 33 and 34. In some embodiments, the tubing 19 is made of a suitable non-toxic material more flexible than the catheter body 12. A suitable material for the tubing 19 is braided polyurethane, i.e., polyurethane with an embedded mesh of braided high-strength steel, stainless steel or the like. The outer diameter of the deflection section 14 is similar to that of the catheter body 12. The size of the lumens is not critical and can vary depending on the specific application.

Various components extend through the catheter 10. In some embodiments, as shown in FIG. 4, the components include lead wire 40T for the tip electrode 17 and lead wires 40D for the discrete electrodes 13 of the sleeve 11. The components also include one or more puller wires 42A and 42B for deflecting the deflection section 14, a cable 44 for an electromagnetic position sensor 46 (see FIG. 6) housed in the distal end section 15. In some embodiments where the catheter 10 is adapted for ablation, the components may also include an irrigation tubing 48 for passing fluid to the distal section 15 and its one or more electrodes. These components pass through the central lumen 18 of the catheter body 12, as shown in FIG. 4.

In the deflection section 14, different components pass through different lumens of the tubing 19 as shown in FIG. 5. In some embodiments, the lead wires 40T and 40D and the sensor cable 44 pass through first lumen 31, a first puller wire 42A passes through second lumen 32, the irrigating tubing 48 passes through third lumen 33, and a second puller wire 42B passes through fourth lumen 34. The second and fourth lumens 32 and 34 are diametrically opposite of each other to provide bi-directional deflection of the intermediate deflection 14.

Figure 6:
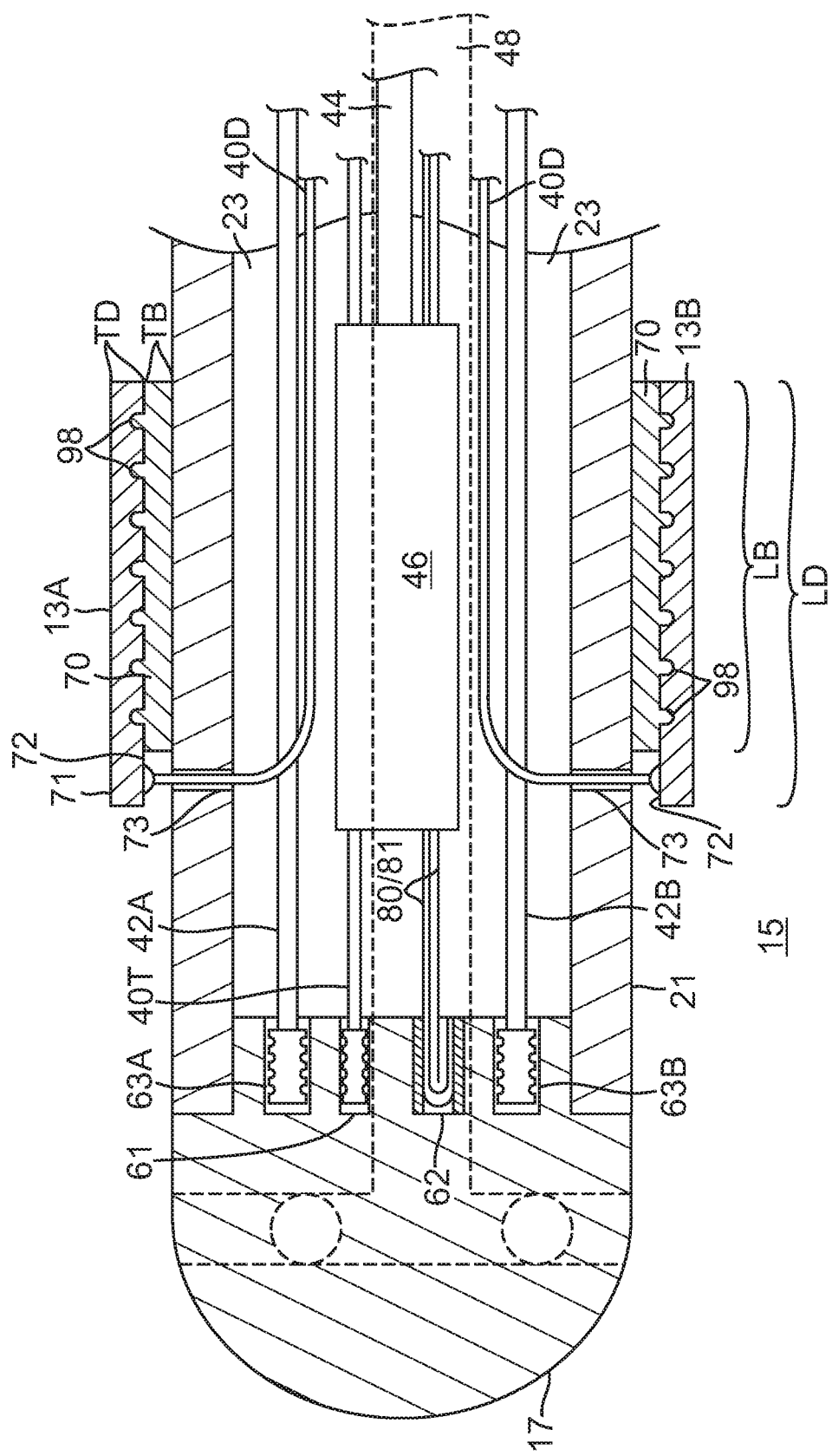
FIG. 6 is a side cross-sectional view of the distal section of FIG. 3.

Distal of the deflection section 14 is the distal end section 15 which includes the tip electrode 17 having a cylindrical configuration with a dome distal tip, as shown in FIG. 3. In some embodiments, the distal end section 15 includes a short section of tubing 21 with a central lumen 23 which houses the position sensor 46 at the distal end of the cable 44, as shown in FIG. 3 and FIG. 6.

The tip electrode 17 mounted on a distal end of the tubing 21 has a diameter generally equal to the outer diameter of the tubing 19. The tip electrode 17 can be made from any suitable material, such as platinum, gold, or stainless steel and, in some embodiments, is preferably made of a platinum-iridium alloy (90% platinum/10% iridium). As shown in FIG. 6, the tip electrode 17 is generally solid. On a proximal face of the tip electrode 17 are a plurality of blind holes, for example, blind holes 61, 62, 63A and 63B. The blind hole 61 receives a distal end of the electrode lead wire 40T which is anchored in the blind hole 61 for electrical connection to the tip electrode 17. The blind hole 62 receives a distal end of a thermocouple wire pair 80/81 which are anchored in the blind hole 62 for sensing temperature of the tip electrode 17. The blind hole 63A receives a distal end of the puller wire 42A and the blind hole 63B receives a distal end of the puller wire 42B for anchoring these puller wires in the tip electrode 17. In the illustrated embodiment, each puller wire is anchored by a metal tubing that is crimped to the distal end of the puller wire and soldered inside the respective blind hole. Anchoring the puller wires within the tip electrode 17 provides additional support for the tip electrode 17 on the flexible plastic tubing 21, reducing the likelihood that the tip electrode 17 will separate from the tubing 21. Alternatively, the puller wires can be attached to sidewall of the tubing 19, for example, with the use of T-bars, as known in the art. Such a design is described in U.S. Pat. No. 9,101,733, the entire disclosure of which is incorporated herein by reference.

Each puller wire 42A and 42B is anchored at its proximal end in the control handle 16. In some embodiments, the puller wires are made of any suitable metal, such as stainless steel or Nitinol, and are preferably coated with Teflon® or the like. The coating imparts lubricity to the puller wires.

A compression coil 52 is situated within the catheter body 12 in surrounding relation to each puller wire 42, as shown in FIG. 4. The compression coils 52 extend from the proximal end of the catheter body 12 to about the proximal end of the deflection section 14. The compression coils 52 are made of any suitable metal, preferably stainless steel. Each compression coil 52 is tightly wound on itself to provide flexibility, i.e., bending, but to resist compression. The inner diameter of the compression coil 52 is preferably slightly larger than the diameter of the puller wire 42. The Teflon® coating on the puller wire 50 allows it to slide freely within the compression coil 52. If desired, particularly if the lead wires 40T and 40D are not enclosed by a protective sheath, the outer surface of the compression coil 52 can be covered by a flexible, non-conductive sheath (not shown), e.g., made of polyimide tubing, to prevent contact between the compression coil 52 and any other wires within the catheter body 12.

The puller wire 42A extends through the second lumen 32 of the tubing 19 and the puller wire 42B extends through the fourth lumen 34 of the tubing 19. Within these lumens, each puller wire extends through a respective plastic, preferably Teflon®, sheath 66 (see FIG. 5), which prevents the puller wires from cutting into the wall of the tubing 19 when the deflection section 14 is deflected.

Longitudinal movement of the puller wires 42 relative to the catheter body 12, which results in deflection of the tip section 14, is accomplished by suitable manipulation of the control handle 16. A suitable control handle design for use with the present invention is described in U.S. Pat. No. 8,287,532, the entire disclosure of which is incorporated herein by reference. If desired, the catheter can be uni-deflectional, i.e., having only one puller wire.

Selected deflection of the intermediate section 14 helps to "steer" the distal end section 15 which supports the tip electrode 17 and the electrode sleeve 11. As shown in FIG. 3, the sleeve 11 includes a circumferential substrate or band 70 supporting a plurality of discrete or "split" electrodes 13 (e.g., 13A and 13B), wherein each electrode on the sleeve 11 is purposefully separated from an adjacent electrode by a space gap G. The space gap G between each pair of adjacent electrodes may be the same or the gap may vary, as desired or appropriate. The band 70 may be constructed of any suitable nonconductive material. In some embodiments, the substrate material may be PEEK, PTFE or polyimide. The discrete electrodes 13 may be constructed of any suitable conductive material. In some embodiments, the material may be platinum—iridium, palladium or MP35N®

With reference to FIG. 3 and FIG. 6, the band 70 has a generally uniform length LB along the longitudinal axis of the catheter, ranging between about 0.5 mm and 5.0 mm, preferably between about 0.6 mm and 2.0 mm, and more preferably having a length equal to about 0.8 mm. The band 70 has a thickness TB in the radial direction ranging between about 0.01 mm and 0.15 mm, preferably between about 0.02 mm and 0.1 mm, and more preferably having a thickness equal to about 0.05 mm. An inner diameter of the band is slightly larger than the outer diameter of the tubing 21 so that the band can be slipped on the tubing 21, for example, from the distal end and advanced proximally to a predetermined location proximal of the tip electrode 17.

Each discrete electrode 13 of the sleeve 11 has a generally uniform thickness TD and each resembles a miniature "tile" with a curved outer surface that together with the outer surface of the other discrete electrodes traces a ring or circumference around the outer surface of the band 70. Accordingly, the sleeve has an atraumatic radial profile that corresponds with the shape of the tubing 21 of the distal section 15 which renders the discrete electrodes particularly well adapted for contacting tissue, especially when the distal section is laid against tissue. Each discrete electrode 13 has a length LD in the longitudinal direction that is greater than the length LB of the band 70 so that each discrete electrode 13 has at least one overhang edge portion 71 that is distal of a distal edge of the band 70 or is proximal of a proximal edge of the band 70. In the illustrated embodiment of FIG. 3 and FIG. 6, each discrete electrode 13 has a distal overhang edge portion 71 relative to the band 70. The portion 71 provides an inner surface 72 facing inwardly toward the outer surface of the band 70, onto which a distal end of a respective lead wire 40D may be conductively attached, for example, by resistance welding. Each lead wire 40D of a discrete electrode 13 passes through a respective aperture 73 formed in the sidewall of the tubing 21, to extend between central lumen 23 and outside of the tubing 21. The aperture 73 is sized and shaped in close conformity to the size and shape of the lead wire so that the aperture 73 may be readily sealed around the lead wire with a suitable sealant.

The dimension or length of each discrete electrode LD along the longitudinal axis of the catheter, ranges between about 0.5 mm and 6.0 mm, preferably between about 1.0 mm and 3.0 mm, and more preferably has a length equal to about 1.0 mm. The thickness TD of each discrete electrode in the radial direction ranges between about 0.02 mm and 0.125 mm, preferably between about 0.02 mm and 0.1 mm, and more preferably has a thickness equal to about 0.05 mm.

It is understood that while the discrete electrodes 13 are illustrated as similarly sized and shaped, they can be sized and/or shaped different from each other. Moreover, the shape of each discrete electrode need not be rectangular as illustrated, but can be any suitable shape, including circular, oval, polygonal, etc.

Figure 7:
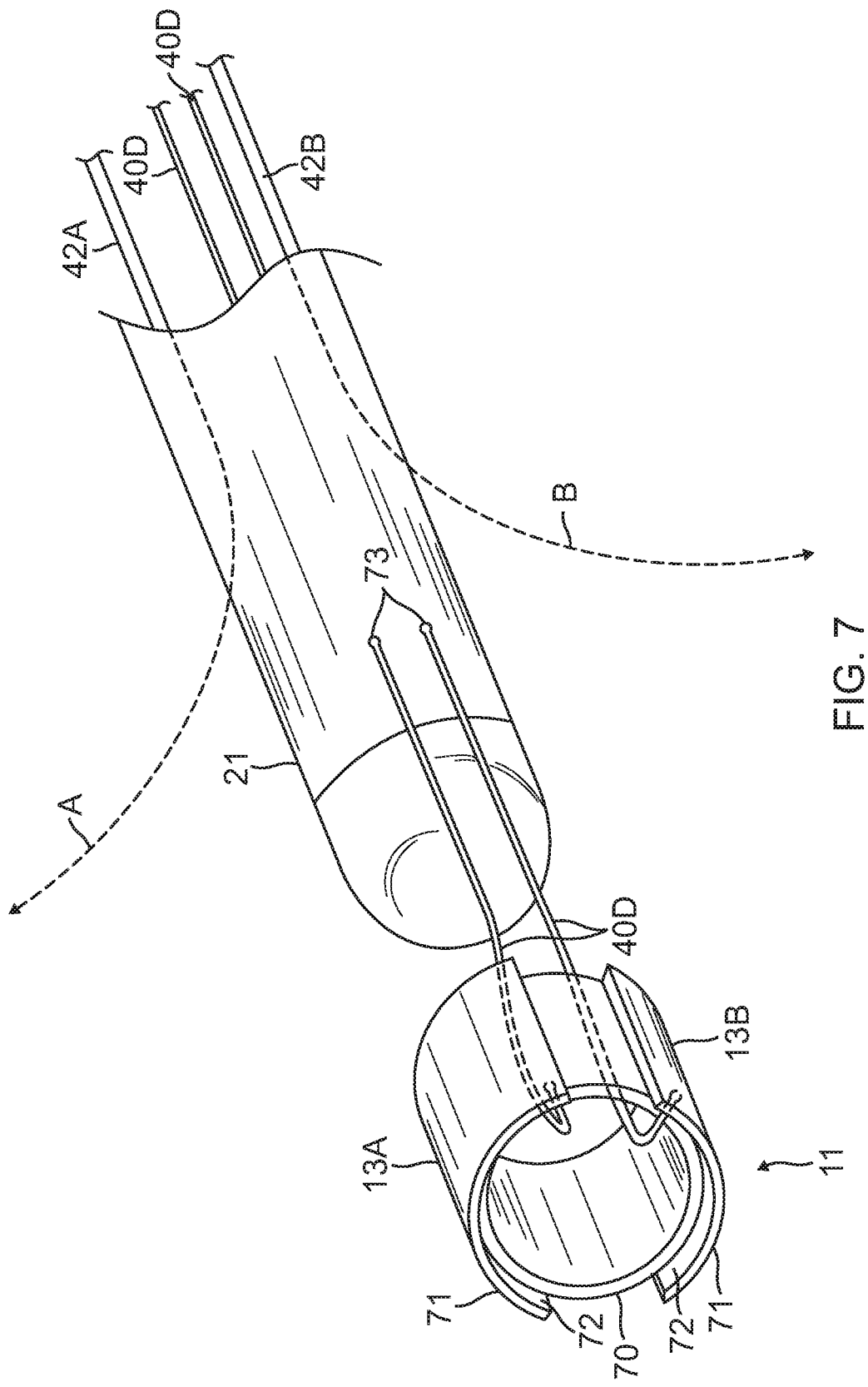
FIG. 7 is a perspective view of the distal section of FIG. 3, during assembly.
Figure 8:
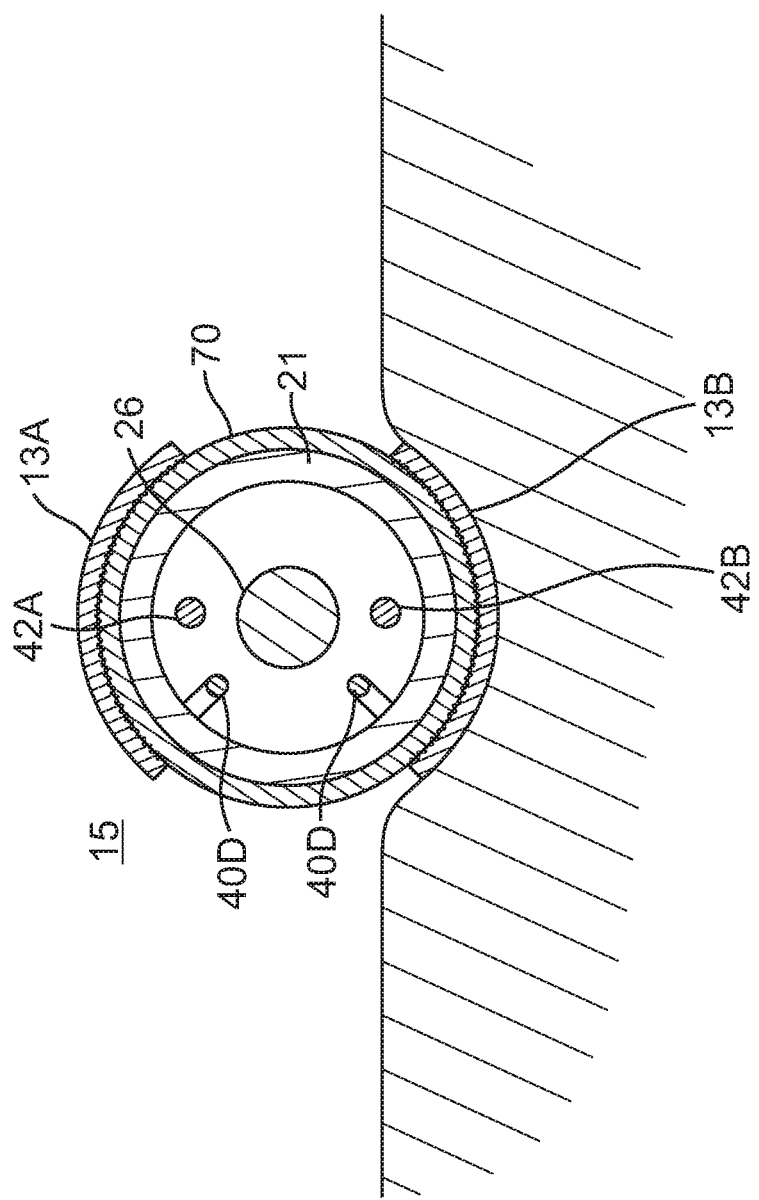
FIG. 8 is an end cross-sectional view of the distal section of FIG. 3, with a selected discrete electrode in contact with tissue.

In some embodiments, the sleeve 11 is oriented circumferentially about the longitudinal axis of the catheter on the distal end section 15 in a manner such that discrete electrodes 13 are generally aligned with deflection direction(s) of the catheter 10. For example, as illustrated in FIG. 3 and FIG. 7, the sleeve 11 has two discrete electrodes 13A and 13B whose circumferential position are aligned with two deflection directions of the catheter (arrows A and B). Deflection directions are dependent primarily on the locations of respective puller wires and their respective lumens. In the illustrated embodiment of FIG. 7, the two deflection directions A and B are diametrically opposite, as determined by diametrically opposite positions of the puller wires 42A and 42B, and their respective lumens 32 and 34 (FIG. 5). As such, one or more selected discrete electrodes 13 may be positioned into contact with tissue by a user deflecting the catheter in a selected direction by actuation of a selected puller wire. In the illustrated embodiment, discrete electrode 13A is deflected into tissue contact by selected actuation of puller wire 42A for deflection of the catheter in direction A. Thus, where the sleeve 11 is radially oriented such that at least one discrete electrode is longitudinally aligned or on the same side of the tubing 21 as a respective puller wire, selective deflection via that puller wire can more place that at least one discrete electrode into tissue contact. Such intended or purposeful orientation of the sleeve during assembly of the catheter and its distal section 15 can therefore provide the catheter with improved predictability and control over placement of one or more discrete electrodes into tissue contact. In FIG. 8, the distal section 15 has been deflected via puller wire 42B to selectively place discrete electrode 13B into contact with tissue, leaving discrete electrode 13A out of tissue contact.

Figure 9:
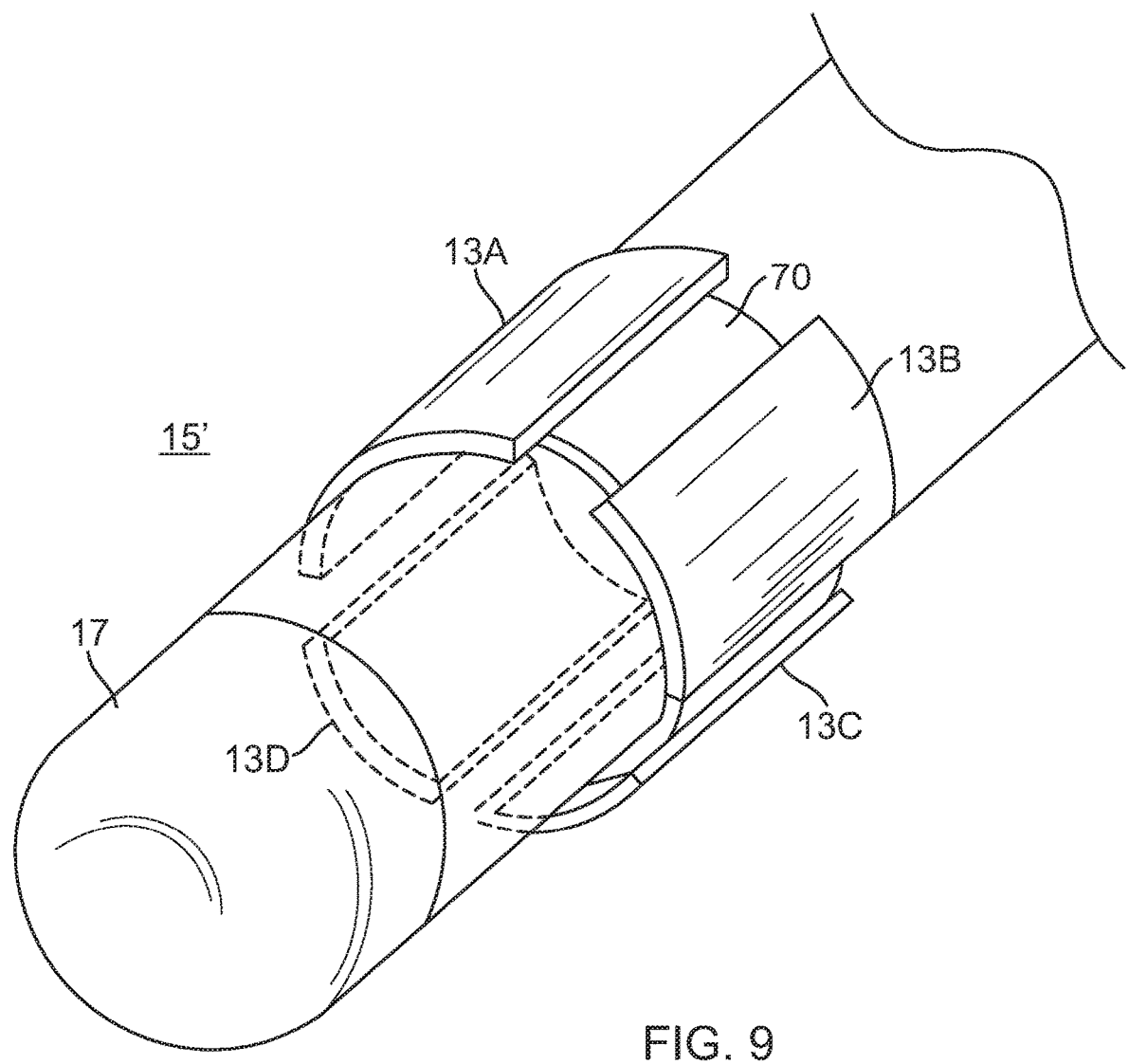
FIG. 9 is a perspective view of a distal section, in accordance with another embodiment.

FIG. 9 illustrates another embodiment of the present invention, having a distal section 15' with a band 70 supporting four discrete electrodes 13A, 13B, 13C and 13D, each spanning about a quadrant around the circumference of the distal section 15'. The distal section 15' may be deflected or otherwise positioned such that one or more discrete electrodes are in contact with tissue with the remaining one or more discrete electrodes being out of contact with tissue.

Method of Assembly:

In some embodiments of the present invention, with reference to FIG. 6 and FIG. 7, a method of assembling a distal section 15 of a catheter includes: providing an electrode sleeve 11 with a band 70 and one or more discrete electrodes, e.g., 13A and 13B; providing a tubing 21 with at least one lumen 23; forming one or more apertures 73 in the sidewall of the tubing 21 to allow communication between the lumen 23 and outside of the tubing 21; passing a lead wire 40D through an aperture 73 to extend between the lumen 23 and outside of the tubing 21; affixing a distal end of the lead wire 40D to a respective discrete electrode 13A and 13D; and mounting the sleeve 11 on the tubing 21 by inserting the distal section through the sleeve 11 and sliding the sleeve onto the distal section.

In more detailed embodiments, the method of assembly includes: providing an electrode sleeve 11 with a band 70 and one or more discrete electrodes 13, wherein a discrete electrode has an overhang edge portion 71; and affixing a distal end of the lead wire 40D to the overhang edge portion 71. In further detailed embodiments, the method of assembly includes affixing the distal end of the lead wire 40D to an inner surface 72 of the overhand edge portion 71.

When connecting distal ends of the lead wires 40D to the discrete electrodes, the lead wires are passed through the center opening of the sleeve 11, s shown in FIG. 7, so that the distal ends of the lead wires can be attached readily attached to the inner surface 72 of the overhang edge portion 71 of each discrete electrode.

The lead wires 40D attached to the discrete electrodes are carefully drawn proximally into the distal section 15 and the catheter so that there is little excess extending outside of the apertures 73 after the sleeve 11 is mounted properly on the distal section 15.

In other more detailed embodiments, the method of assembly includes affixing the distal end of the lead wire 40D to the overhand edge portion 71 at a location that is radially aligned with a respective aperture 73, as shown in FIG. 7.

In other more detailed embodiments, the mounting the sleeve 11 on the tubing 21 includes longitudinally aligning one or more discrete electrodes 13 with one or more deflection directions of the catheter (see arrows A and B). In more detailed embodiments, the mounting the sleeve 11 on the tubing 21 includes longitudinally aligning one or more discrete electrodes with a puller wire of the catheter, as shown in FIG. 7.

The inner surface 72 of the overhang edge portion 71 is exposed and provides an optimal location and welding surface for conductive welding of the lead wire to the band 70 of the electrode sleeve 13. Medical grade adhesive, e.g., polyurethane, is applied to fix the sleeve 13 on the tubing 21.

Figure 10:
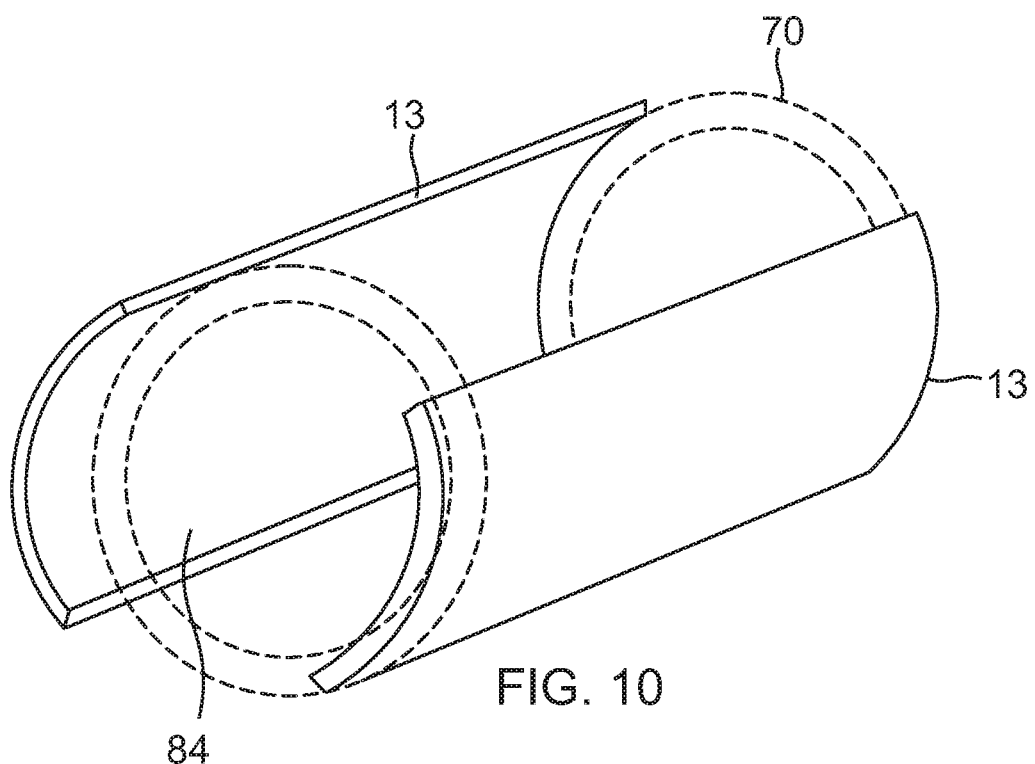
FIG. 10 is a perspective view of an electrode sleeve, in accordance with an embodiment.
Figure 11:
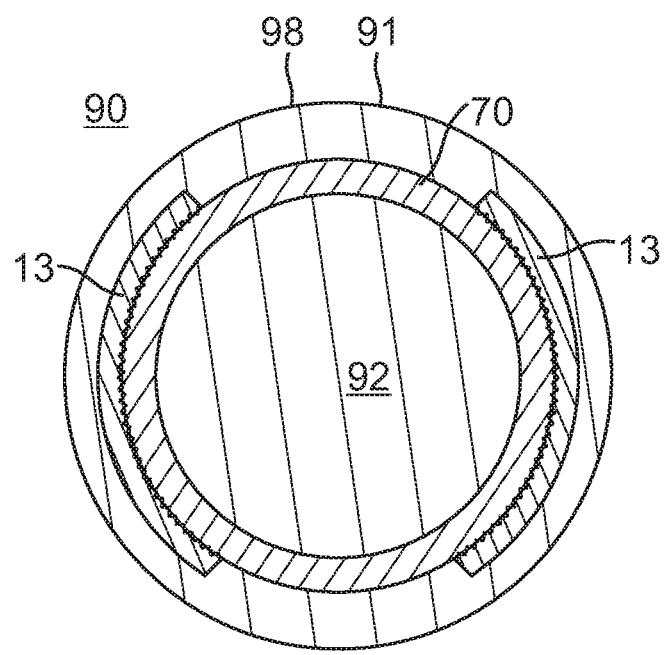
FIG. 11 is an end-cross sectional view of a die for manufacturing the electrode sleeve of FIG. 10, in accordance with an embodiment.

Method of Manufacturing Electrode Sleeve with Insert-Molding:

The present invention is also directed to a method of manufacturing the sleeve that includes insert-molding the band 70 onto the discrete electrodes 13 (as the base material) to form the sleeve 11, as shown in FIG. 10. In some embodiments, the method employs a die 90, as shown in FIG. 11, which includes a hollow cylindrical outer die member 91 and an inner cylindrical (solid or hollow) die member 92 between which is a space to be filled by an insert-molding material suitable for forming the band 70. Suitable material for insert-molding includes thermoplastics, such as PEEK, PTFE or polyimide. An underside 84 of the discrete electrodes 13 may be coated with adhesives before the insert-molding material is added to the die 90, or the underside 84 may be scored, textured, or altered slightly with projections or recessions 98 (as best shown in FIG. 6) to facilitate attachment to the insert-molding material.

The outer surface of inner die member 92 has a smooth or circular cross-section so that the band 70 has a smooth inner surface. The inner surface of the outer die member 91 has raised surfaces 98 extending between adjacent discrete electrodes 13, as shown in the embodiment of FIG. 11, so that outer surfaces of the discrete electrodes 13 are raised relative to the outer surface of the band 70, as shown in the embodiment of FIG. 10.

Laser cutting may be used to customize or finish the shape and size of each discrete electrode 13 on the band 70. It is understood that the discrete electrodes may be formed as a ring on the band that is subsequently laser cut into any split electrode configuration as appropriate or desired.

Figure 12:
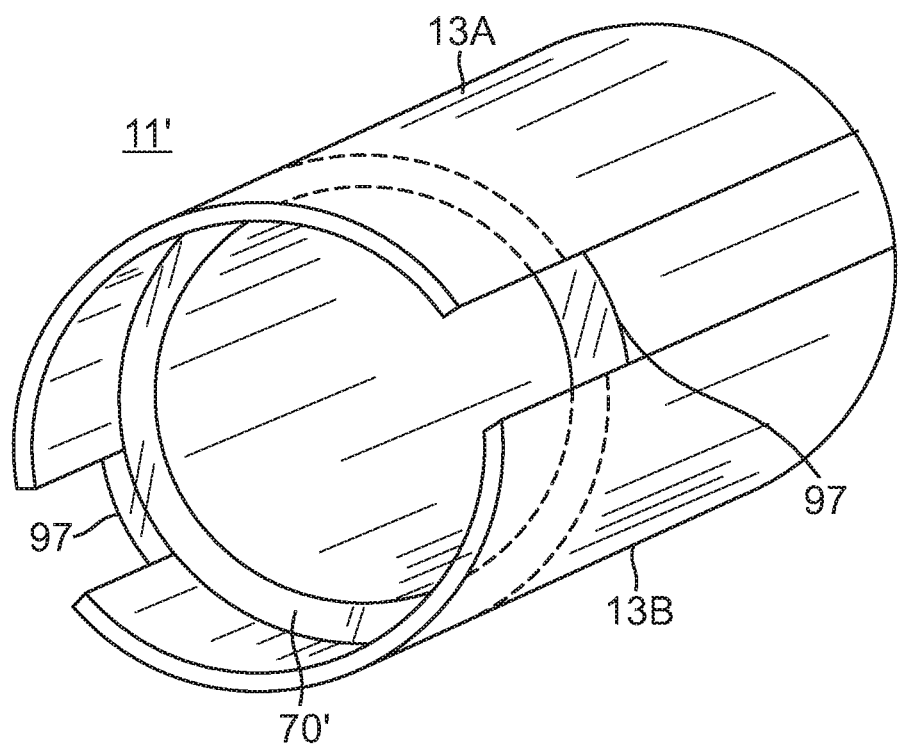
FIG. 12 is a perspective view of an electrode sleeve, in accordance with another embodiment.

Method of Manufacturing Electrode Sleeve with Over-Molding:

In some embodiments of the present invention, a method of manufacturing a sleeve 11' includes over-molding the discrete electrodes 13 onto a band 70 (as the base material) to form the sleeve 11', as shown in FIG. 12. In some embodiments, the discrete electrodes 13 are formed by metal injection molding (MIM), also referred to as Powdered Injection Molding (PIM), onto the band. MIM is typically used for manufacturing small, complex parts that otherwise would require extensive finish machining if made by other metal-forming processes. MIM is a repeatable process for components made from high-temperature alloys. MIM parts are nearly fully dense, which gives excellent mechanical properties and allows secondary operations, for example, heat treating and machining to be easily performed. MIM/PIM involves forming a feedstock using very fine metal powders that are typically mixed with a primary paraffin material and a secondary thermoplastic polymer which act as binders. Suitable metals for forming the metal powders include, for example, platinum, iridium, palladium, and MP35N, or combinations of same. Using powder particulars typically less than 15-20 micros, MIM can achieve 95-100% theoretical density, thus allowing close tolerances and reducing costs by producing small, complex parts over high production runs. The feedstock is then molded by being fed into a suitable molding equipment, heated and injected into a mold cavity under high pressure. The "green part" produced by the molding process is subjected to a "debinding" process where the binders are removed, for example, extracted by thermal or solvent processing. When debinding is complete, the part is referred to as a "brown part." The brown part is then subjected to a sintering process (solid-state diffusion) in a controlled-atmosphere furnace where the part is heated close to its melting point and the remaining binder is eliminated, giving the part its final geometry.

A method of manufacturing the sleeve that includes over-molding the MIM discrete electrodes 13 onto the band 70 to form sleeve 11', employs a die 100, as shown in FIG. 12, which includes a hollow cylindrical outer die member 94 and an inner cylindrical (solid or hollow) die member 99 between which is a space to be filled by a material suitable, as described above, for forming the discrete electrodes 13 (e.g., 13A and 13B). Portions of the outer surface of the band 70 onto which the MIM discrete electrodes are affixed may be textured for better adhesion or attachment between the electrodes and the band.

Figure 13:
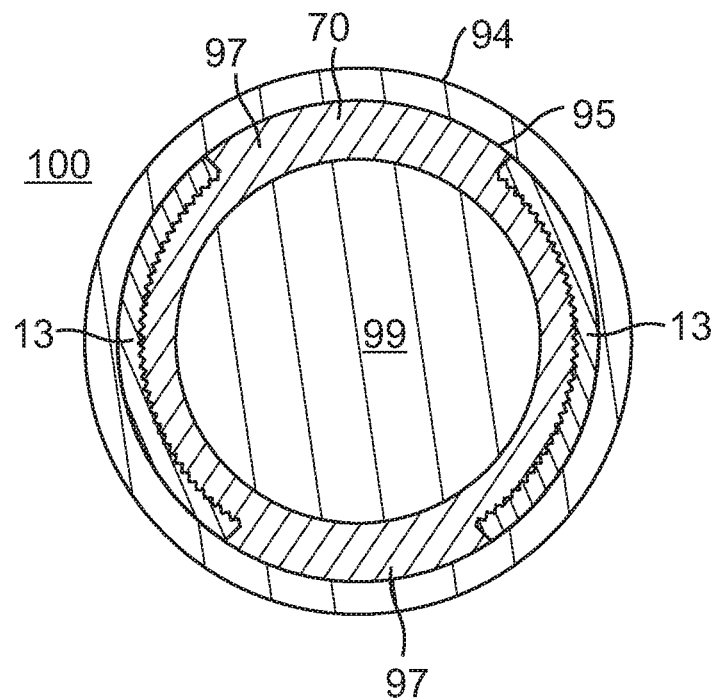
FIG. 13 is an end-cross-sectional view of a die for manufacturing the electrode sleeve of FIG. 12, in accordance with an embodiment.

As shown in the embodiment of FIG. 13, the outer surface of inner die member 99 has a smooth or circular cross-section so that the band 70 has a smooth inner surface. The inner surface of the outer die member 94 has a smooth or circular cross-section so that the over-molded band 70 is formed with raised surfaces 97 that extend between and are flush with adjacent discrete electrodes 13 (e.g., 13A and 13B), as shown in FIG. 12.

Notably, whether the sleeve is formed by injection-molding or over-molding, the respective die may be formed as desired or appropriate to provide a sleeve with raised discrete electrodes relative to an outer surface of the band 70 (as shown in FIG. 10) or a sleeve with discrete electrodes that are flush with the outer surface of the band 70 (as shown in FIG. 12).

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. An electrophysiology catheter comprising:
   an elongated body;
   a distal section distal of the elongated body; and
   an electrode sleeve mounted on the distal section, the electrode sleeve comprising:
   a band extending circumferentially around the distal section, the band constructed of an electrically-non-conductive material;
   a plurality of discrete electrodes affixed to the band, each occupying a different radial position around the band.

2. The catheter of claim 1, wherein each discrete electrode has overhang edge portion to provide a surface for lead wire attachment.

3. The catheter of claim 1, wherein the plurality of discrete electrodes ranges between about two and eight.

4. The catheter of claim 1, further comprising a puller wire, wherein the puller wire extends through the body and is longitudinally aligned with at least one discrete electrode.

5. The catheter of claim 4, further comprising a control handle, the control handle configured to actuate the puller wire for deflecting the catheter.

6. The catheter of claim 1, wherein each discrete electrode has a curved outer surface and the plurality of discrete electrodes are arranged on the band such that their curved outer surfaces trace a circumference around the band.

7. An electrophysiology catheter comprising:
   an elongated body;
   a deflection section distal of the elongated body;
   a distal section distal of the elongated body, the distal section having a tubing with a sidewall;
   an electrode sleeve mounted on the distal section, the electrode sleeve comprising an electrically-nonconductive band and a plurality of discrete electrodes, the band extending circumferentially around the distal section, each discrete electrode occupying a different radial position around the band; and
   a plurality of lead wires extending through the elongated body and the deflection section, and into the distal section, each lead wire passing through a respective aperture formed in the sidewall of the tubing of the distal section, each wire being connected at its distal end to a respective discrete electrode.

8. The catheter of claim 6, wherein each discrete electrode has an overhang edge portion and each lead wire is attached at its distal end to a respective overhang edge portion.

9. The catheter of claim 7, wherein the plurality of discrete electrodes ranges between about two and eight.

10. The catheter of claim 7, further comprising a puller wire, wherein the puller wire extends through the body and is longitudinally aligned with at least one discrete electrode.

11. The catheter of claim 10, further comprising a control handle, the control handle configured to actuate the puller wire for deflecting the catheter.

* * * * *